(12) United States Patent
Del Seppia et al.

(10) Patent No.: US 9,090,544 B2
(45) Date of Patent: Jul. 28, 2015

(54) PROCESS FOR THE PRODUCTION OF 1,3-BUTADIENE

(71) Applicant: versalis S.p.A., San Donato Milanese (MI) (IT)

(72) Inventors: Alessandro Del Seppia, Porto Mantovano (IT); Fabio Assandri, Mantova (IT); Elena Ghirardo, Mantova (IT); Carmelo Vella, Curtatone (IT)

(73) Assignee: versalis S.p.A., San Donato Milanese (IT)

( * ) Notice: Subject to any disclaimer, the term of this patent is extended or adjusted under 35 U.S.C. 154(b) by 0 days.

(21) Appl. No.: 14/366,416

(22) PCT Filed: Dec. 24, 2012

(86) PCT No.: PCT/IB2012/057689
§ 371 (c)(1),
(2) Date: Jun. 18, 2014

(87) PCT Pub. No.: WO2013/098760
PCT Pub. Date: Jul. 4, 2013

(65) Prior Publication Data
US 2015/0005532 A1 Jan. 1, 2015

(30) Foreign Application Priority Data
Dec. 28, 2011 (IT) .............. MI2011A2404

(51) Int. Cl.
| | |
|---|---|
| *C07C 41/09* | (2006.01) |
| *C07C 5/32* | (2006.01) |
| *C07C 41/06* | (2006.01) |
| *C07C 5/333* | (2006.01) |
| *C07C 7/08* | (2006.01) |

(52) U.S. Cl.
CPC .............. *C07C 41/09* (2013.01); *C07C 5/322* (2013.01); *C07C 5/3332* (2013.01); *C07C 5/3335* (2013.01); *C07C 5/3337* (2013.01); *C07C 7/08* (2013.01); *C07C 41/06* (2013.01); *C07C 2521/04* (2013.01); *C07C 2521/08* (2013.01); *C07C 2523/02* (2013.01); *C07C 2523/04* (2013.01); *C07C 2523/08* (2013.01); *C07C 2523/14* (2013.01); *C07C 2523/42* (2013.01); *C07C 2523/62* (2013.01); *C07C 2523/63* (2013.01)

(58) Field of Classification Search
None
See application file for complete search history.

(56) References Cited

U.S. PATENT DOCUMENTS

| 4,054,613 | A | 10/1977 | Haskell et al. | |
|---|---|---|---|---|
| 2007/0167661 | A1 | 7/2007 | Johann et al. | |
| 2008/0183024 | A1* | 7/2008 | Klanner et al. | 585/633 |
| 2009/0088594 | A1* | 4/2009 | Oh et al. | 585/627 |
| 2010/0121123 | A1* | 5/2010 | Chung et al. | 585/629 |

FOREIGN PATENT DOCUMENTS

WO WO 2005/063658 A1 7/2005

OTHER PUBLICATIONS

International Search Report and Written Opinion issued Mar. 14, 2013 in PCT/IB2012/057689.

* cited by examiner

*Primary Examiner* — Brian J Davis
(74) *Attorney, Agent, or Firm* — Oblon, McClelland, Maier & Neustadt, L.L.P.

(57) ABSTRACT

The present invention relates to a process for the production of 1,3-butadiene which comprises the following phases: a) extracting, by means of extractive distillation, in an extraction section, an end-product containing 1,3-butadiene and a raffinate product, starting from mixtures of saturated and unsaturated compounds having from 2 to 10 carbon atoms in the chain; b) sending the raffinate product to a dehydrogenation section; c) dehydrogenating the raffinate product in the dehydrogenation section in the presence of a dehydrogenation catalyst and an inert product so as to form a reaction effluent containing 1,3-butadiene; d) recirculating the reaction effluent containing 1,3-butadiene directly to the extraction section after separating the incondensable compounds.

18 Claims, 3 Drawing Sheets

PROCESS FOR THE PRODUCTION OF 1,3-BUTADIENE

This application is a 371 of PCT/IB2012/057689, filed Dec. 24, 2012. Priority to Italian patent application MI2011A002404, filed Dec. 28, 2011, is claimed.

The present invention relates to a process for the production of 1,3-butadiene starting from a mixture of saturated and unsaturated compounds having from 2 to 10 carbon atoms in the chain, in the text mentioned as $C_2$-$C_{10}$, preferably mixtures of butanes and butenes, in the text indicated as $C_4$. More specifically, said process and apparatus can be applied to mixtures of butanes and butenes produced by cracking plants, both stand-alone and integrated with a selective extraction plant of 1,3-butadiene or with the entire upgrading chain of $C_4$.

The strong increase in the request for elastomeric products registered on the world market, drawn by the expansion of fields such as the automotive industry, has consequently led to an ever-increasing demand for 1,3-butadiene, used as raw material for the production of a large range of synthetic rubbers (for example, polybutadiene, or SBR, SBS, NB) and polymeric resins (for example ABS, PEN).

A large part of 1,3-butadiene is currently produced industrially by extractive distillation of the $C_4$ fraction produced in Steam Crackers, whereas the remaining part is produced by dehydrogenation of butanes, according to the Catadiene™ process of CB&I Lummus Technology, or $C_4$ olefins according to the Oxo-D™ process of Petro-Tex, currently Texas Petrochemicals, with subsequent extractive distillation of the effluent obtained. A description of the various technologies mentioned can be found in Perp Report Nexant Chem Systems Butadiene/Butylenes 09/10-5.

The production of 1,3-butadiene by extractive distillation has, as an intrinsic limit, the availability of the C4 feedstock coming from cracking furnaces, in prospect becoming increasingly more limited following the shift of naphtha feedstocks to gas, whereas dehydrogenation technologies starting from $C_4$ paraffins and/or olefins are non-competitive with respect to the selective extraction of the $C_4$ fraction from cracking.

In particular, due to the significant investment cost required by the reaction section and the necessary extraction plant downstream, the Catadiene™ process has limited industrial applications, as is also greatly limited the industrial appeal of the Oxo-D™ technology in which, in addition to an already considerable investment cost which jeopardizes its application especially for small capacities, there are also significant safety problems relating to the very nature of the process.

U.S. Pat. No. 6,187,985 describes a dehydrogenation process of $C_2$-$C_{22}$ paraffins (having from 2 to 22 carbon atoms in the chain) wherein the dehydrogenation of the $C_5$ products can be used for upgrading the low-boiling aliphatic hydrocarbons, such as pentanes and iso-pentanes, which are recovered after the extraction of unsaturated compounds from the $C_5$ fractions of steam cracking and catalytic cracking processes.

US 2010/0168493 describes a dehydrogenation process of light paraffins, wherein said dehydrogenation can be used for upgrading the low-boiling aliphatic hydrocarbons, such as pentanes and iso-pentanes, which are recovered after the extraction of unsaturated compounds from the $C_5$ fractions of steam cracking and catalytic cracking processes.

The Applicant has now found an innovative process, potentially applicable to a conventional plant for the selective extraction of 1,3-butadiene, already existing or newly produced, for the production of 1,3-butadiene starting from a mixture of saturated and unsaturated compounds having from 2 to 10 carbon atoms in the chain, preferably mixtures of butanes and butenes. The primary advantage of this innovative process is to allow an increase in the extraction yield of 1,3-butadiene.

An object of the present invention therefore relates to a process for the production of 1,3-butadiene comprising the following phases:

a) extracting, by means of extractive distillation, in an extraction section, an end-product containing 1,3-butadiene and a raffinate product, starting from mixtures of saturated and unsaturated compounds having from 2 to 10 carbon atoms in the chain;

b) sending the refined extraction product to a dehydrogenation section;

c) dehydrogenating the raffinate product in the dehydrogenation section in the presence of a dehydrogenation catalyst and an inert product so as to form a reaction effluent containing 1,3-butadiene;

d) recirculating the reaction effluent containing 1,3-butadiene directly to the extraction section after separating the incondensable compounds.

The innovative and enhanced process configuration, object of the present invention, overcomes the restrictions associated with the supply methods of 1,3-butadiene currently commercialized, as mentioned above, by increasing the recovery of 1,3-butadiene from traditional extraction plants, by the addition of a dehydrogenation section of raffinate products or extractive distillation products, considering the same $C_4$ mixture feed stream.

A comparison method applied in the state of the art is to fully hydrogenate the raffinate products to paraffins and recycle them to co-cracking in substitution of the corresponding aliquot of the total naphtha feedstock required, thus upgrading the raffinate products and increasing the plant potentiality with the same fresh naphtha fed. The process, object of the present invention, shifts the advantage from the lower consumption of fresh naphtha in the steam cracking or, alternatively, from an increase in productions within the range of cracking products, to an increase in the production of 1,3-butadiene, allowing a specific maximization of the recovery of this component from the $C_4$ streams.

The present invention therefore overcomes the potential limitation imposed by the availability of the $C_4$ fraction from cracking, without having to resort to creating a stand-alone plant for the production of butadiene from dehydrogenation, which is more demanding in terms of investment cost and more critical from the point of view of safety and operating management. The limited increase in investment required for increasing the capacity of the extraction section and guaranteed by the scale factor, together with a limited investment cost of the dehydrogenation unit alone, guarantee the economical convenience, also on a small scale, of the process solution, object of the present invention.

Further objectives and advantages of the present invention will appear more evident from the following description and enclosed figures, provided for purely illustrative and non-limiting purposes.

DETAILED DESCRIPTION

Figure 1:
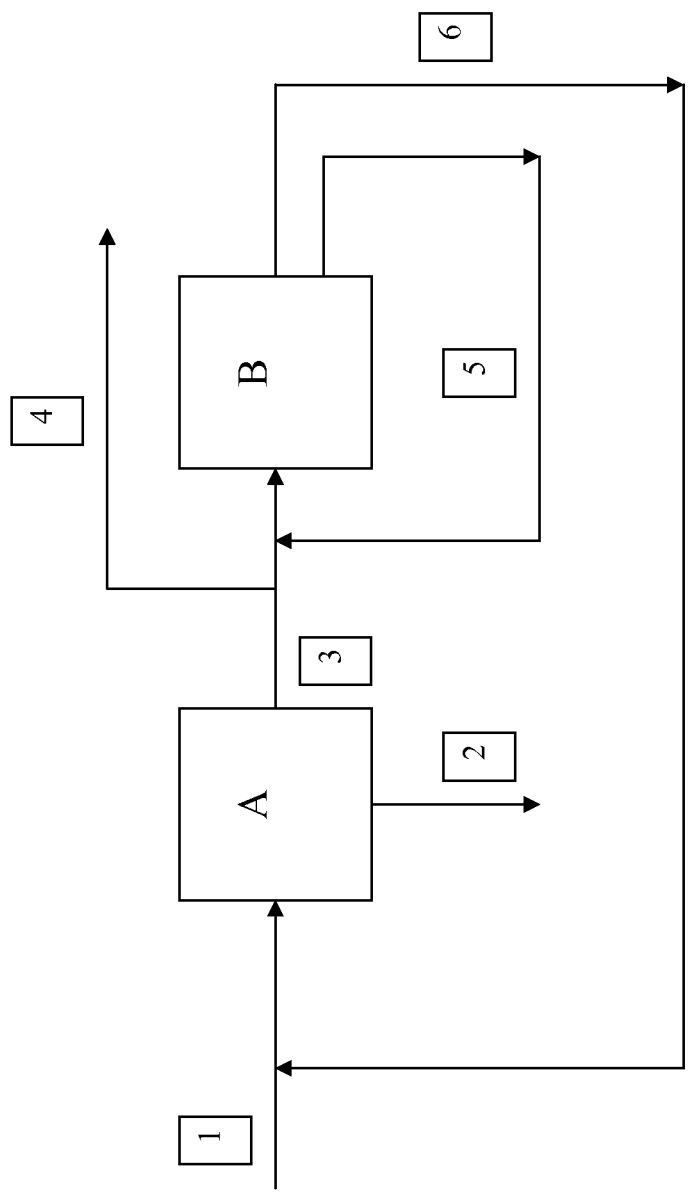
FIG. 1 illustrates an embodiment of the present invention, wherein A is an extractive distillation section of 1,3-butadiene, B is a dehydrogenation section of the raffinate product, 1 is a mixture containing saturated and unsaturated $C_4$ compounds, 2 is the final product containing 1,3-butadiene, 3 is the raffinate product, 4 is a possible purge of the raffinate product, 5 is the recycled stream rich in butanes and butenes, 6 is the recycled stream rich in 1,3-butadiene.
Figure 2:
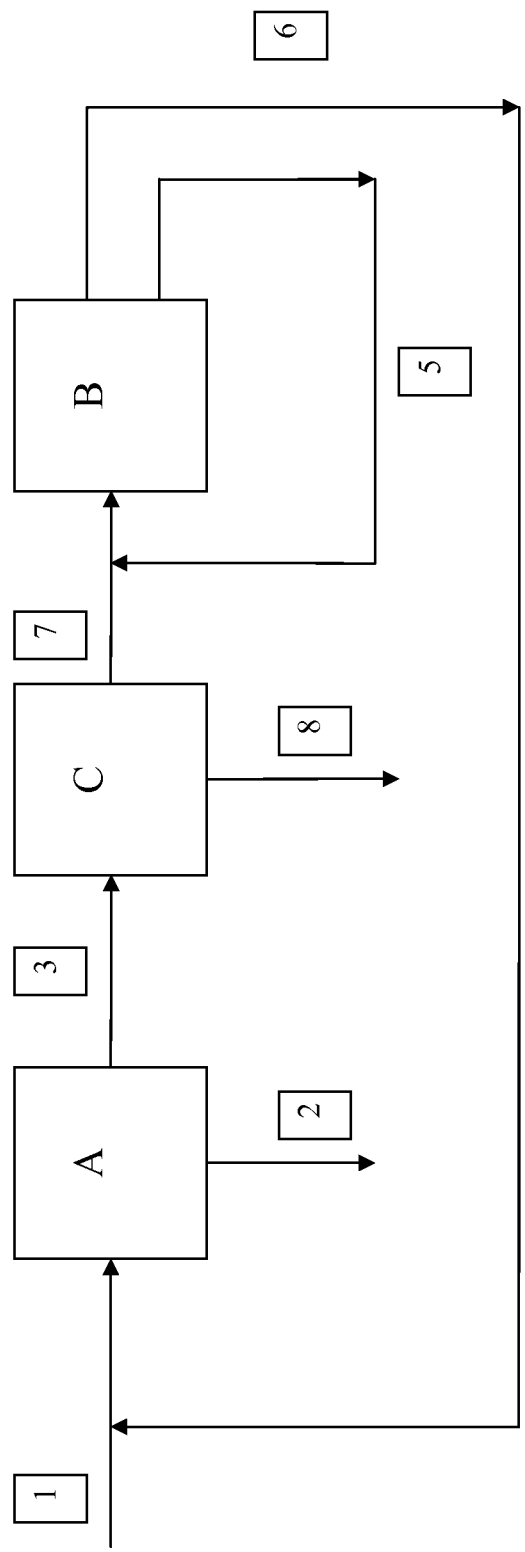
FIG. 2 illustrates an embodiment of the present invention wherein, in addition to the elements and streams identical to those of FIG. 1, C is an etherification section, 7 is the stream of raffinate 2, 8 is the stream of Ethyl Tert Butyl Ether.

In an embodiment, the present invention relates to a process for the production of 1,3-butadiene comprising the following phases:
a) extracting, by means of extractive distillation, in an extraction section, an end-product containing 1,3-butadiene and a raffinate product, starting from mixtures of saturated and unsaturated compounds having from 2 to 10 carbon atoms in the chain;
b) sending the raffinate product to a dehydrogenation section;
c) dehydrogenating the raffinate product in the dehydrogenation section in the presence of a dehydrogenation catalyst and an inert product so as to form a reaction effluent containing 1,3-butadiene;
d) recirculating the reaction effluent containing 1,3-butadiene directly to the extraction section after separating the incondensable compounds.

In a further embodiment of the present invention, the effluent of the dehydrogenation reaction, enriched in 1,3-butadiene, after separation of the non-condensable products, is separated, for example by means of conventional distillation, into a stream rich in 1,3-butadiene and a stream containing the non-reacted saturated and unsaturated compounds having from 2 to 10 carbon atoms in the chain. In this case, the stream rich in 1,3-butadiene is sent back to the extraction section as recycled product. After separation, the stream containing the non-reacted saturated and unsaturated compounds having from 2 to 10 carbon atoms in the chain is preferably recirculated to the dehydrogenation section.

A mixture of saturated and unsaturated compounds having from 2 to 10 carbon atoms in the chain, indicated in the text as $C_2$-$C_{10}$, preferably a mixture of butanes and butenes, is fed to the extractive distillation section, from which a final product containing 1,3-butadiene and a raffinate product are obtained, containing saturated and unsaturated $C_2$-$C_{10}$ compounds, preferably butanes and butenes.

The raffinate product is subsequently fed to the catalytic dehydrogenation section to form a reaction effluent containing 1,3-butadiene and the saturated and unsaturated compounds having from 2 to 10 carbon atoms. This effluent is preferably separated to give a product rich in 1,3-butadiene and a stream rich in non-reacted saturated and unsaturated compounds.

At this point, the concentrated product, or rich in 1,3-butadiene, is sent to the extraction section, minimizing the possible overall impact in terms of increase in the capacity required to the extraction section. It is, in fact, preferable not to overburden the extraction section which may not have the necessary capacity for treating the whole reaction effluent coming from the dehydrogenation section.

The mixture rich in saturated and unsaturated compounds, such as, preferably, non-reacted butanes and butenes, is sent to the dehydrogenation section as recycled product.

Preferably the process object of the present invention may also include an etherification phase subsequent to the extraction phase and preceding the dehydrogenation phase.

In this way, the raffinate product can be subjected to etherification of the iso-butene with ethanol or methanol to obtain Ethyl Tert Butyl Ether (ETBE) or Methyl Tert Butyl Ether (MTBE) and a fraction indicated in the text as raffinate 2, which can be fed to the dehydrogenation section to give an intermediate product rich in 1,3-butadiene, or sent to a further purification section, thus separating 1-Butene from a fraction called raffinate 3. According to this latter embodiment, the raffinate 3 can be sent to the dehydrogenation section, to give an intermediate product concentrated in 1,3-butadiene. The dehydrogenation section, object of the present invention, can be fed with a stream selected from the raffinate product, raffinate 2, raffinate 3, or mixtures thereof.

A preferred dehydrogenation catalyst is a catalytic composition comprising microspheroidal alumina and an active component containing a mixture comprising Gallium and/or Gallium oxides, Tin and/or Tin oxides, Platinum and/or Platinum oxides, and oxides of alkaline and/or alkaline-earth metals.

The microspheroidal alumina carrier is preferably modified with silica which is particularly suitable in fluid-bed or "Fast Riser" dehydrogenation reactors. The Gallium oxides are more preferably selected from $Ga_2O_3$, $Ga_2O$ or mixtures thereof; the Tin oxides are more preferably selected from $SnO$, $SnO_2$ or mixtures thereof; the Platinum oxides are more preferably selected from $PtO$, $PtO_2$ or mixtures thereof; finally, more preferably an oxide of alkaline metals is $K_2O$.

Said catalytic composition surprisingly allows the yield to 1,3-butadiene to be maximized, contemporaneously reducing the investment cost associated with the plant configuration (apparatus), object of the present invention, as said catalytic composition is extremely active and selective.

The quantity of Gallium and/or Gallium oxides preferably ranges from 0.1% by weight to 34% by weight, more preferably from 0.2% by weight to 3.8% by weight, with respect to the total weight of the catalytic composition.

The quantity of alkaline and/or alkaline-earth metals preferably ranges from 0.05% by weight to 5% by weight, more preferably from 0.2% by weight to 3.8% by weight, with respect to the total weight of the catalytic composition.

The quantity of Tin and/or Tin oxides preferably ranges from 0.001% by weight to 1% by weight, more preferably from 0.05% by weight to 0.4% by weight, with respect to the total weight of the catalytic composition.

The concentration of platinum preferably ranges from 1 ppm to 500 ppm by weight, preferably from 1 ppm to 99 ppm by weight, even more preferably from 1 to 50 ppm, with respect to the total weight of the catalytic composition.

The quantity of silica present in the carrier ranges from 0.05% by weight to 5% by weight, more preferably from 0.03% by weight to 3% by weight, with respect to the total weight of the catalytic composition, the rest being alumina. Preferably the surface area of the microspheroidal alumina is lower than or equal to 150 $m^2/g$.

More preferably the concentration of $Ga_2O_3$ ranges from 0.1% by weight to 34% by weight, more preferably from 0.2% by weight to 3.8% by weight, with respect to the total weight of the catalytic composition.

More preferably the quantity of $K_2O$ ranges from 0.05% by weight to 5% by weight, more preferably from 0.1% by weight to 3% by weight, with respect to the total weight of the catalytic composition.

More preferably the quantity of SnO ranges from 0.001% by weight to 1% by weight, more preferably from 0.05% by weight to 0.4% by weight, with respect to the total weight of the catalytic composition.

The quantity of platinum preferably ranges from 1 ppm to 500 ppm by weight, preferably from 1 ppm to 99 ppm by weight, more preferably from 1 ppm to 50 ppm with respect to the total weight of the catalytic composition.

A further preferred dehydrogenation catalyst contains a quantity ranging from 0.1% by weight to 33.6% by weight of $Ga_2O_3$, from 1 ppm to 99 ppm of platinum, a quantity of 0% by weight to 5% by weight of oxides of alkaline and/or alkaline earth metals and an alumina carrier modified with a quantity of silica ranging from 0.08% by weight to 3% by weight.

The dehydrogenation section comprises at least one fluid-bed dehydrogenation reactor and separately, at least one regenerator for restoring the activity of at least part of the dehydrogenation catalyst, preferably the catalytic composition described and claimed in the present text. The dehydrogenation catalyst is kept in circulation between the reactor and regenerator: once regenerated, it can be recirculated to the dehydrogenation section.

The catalytic composition is always recirculated between the reaction section and a regenerator and vice versa, using a carrier gas. The same carrier gas can be used for diluting the feedstock at the inlet of the reaction section. The inert product for diluting the feedstock can be selected from nitrogen, methane, or another fuel gas with a maximum hydrogen content equal to 1% by weight.

The dehydrogenation section preferably requires the use of a Fast-Riser-type reactor, as it considerably improves the performances of the catalyst and in particular the catalytic composition described in the present text: this type of reactor allows to exploit the low contact times, with the same performances, and significantly reduce the reduction of the reaction volumes.

The dehydrogenation phase operates at a temperature ranging from 450° C. to 700° C. and at a pressure ranging from 0.2 atm absolute to 2 atm.

If the dehydrogenation is carried out in a Fast-Riser-type reactor, the residence time of the gas phase is less than a minute, and preferably ranges from 0.2 sec. to 5 sec.

The regeneration of the dehydrogenation catalyst is preferably effected in a fluid bed at a temperature higher than the operating temperature of the reactor, preferably higher than 700° C. The pressure in the regenerator is slightly higher than atmospheric pressure. The residence time of the catalyst during the regeneration ranges from 5 to 60 minutes, preferably from 20 to 40 minutes. During the regeneration, the hourly space velocity of the gas phase (GHSV in Nl/h air per liter of catalyst) ranges from 1,000 to 5,000 $h^{-1}$, preferably from 2,000 to 3,000 $h^{-1}$.

EXAMPLE 1

The overall yield to 1,3 butadiene of an integrated system comprising an extractive distillation plant of 1,3 butadiene is determined hereunder, starting from a mixture of $C_4$ olefins and paraffins from a steam cracker and a dehydrogenation plant for the upgrading of the refined extraction product by recycling a dehydrogenated stream rich in 1,3 butadiene to the extraction section, according to a scheme described hereunder and illustrated in FIG. 1.

A mixture of $C_4$ olefins and paraffins produced by a steam cracker is fed to the extraction unit of 1,3 butadiene and the raffinate product leaving this section is subsequently fed to a catalytic dehydrogenation unit, from which a stream rich in butadiene is obtained, which is recycled to the extraction unit, and a stream of non-reacted butanes and butenes which is recycled to the dehydrogenation reactor, except for a modest purge of $C_{5+}$ compounds.

The $C_4$ mixture in the feed to the plant is equal to 33.8 ton/h and the composition of the stream is indicated in Table 1.

TABLE 1

| Light products and C2-C3 [% w/w] | 0.2 |
| n-Butane [% w/w] | 3.9 |
| i-Butane [% w/w] | 0.2 |
| i-Butene [% w/w] | 24.6 |
| 1-Butene [% w/w] | 11.7 |
| cis2-Butene [% w/w] | 3.9 |
| tr2-Butene [% w/w] | 5.3 |
| 1,3-Butadiene [% w/w] | 49.2 |
| 1,2-Butadiene [% w/w] | 0.1 |
| C4+ [% w/w] | 0.9 |

In the case of a stand-alone butadiene extraction plant, i.e. without the dehydrogenation section downstream, with yields typical of industrially applied technologies, a stream of 1,3 butadiene equal to 16.5 ton/h is produced together with a stream of raffinate product equal to 16.3 ton/h.

In the case of integration of the butadiene extraction unit with the dehydrogenation unit of the raffinate 1 (see FIG. 1), on the other hand, 28.3 ton/h of 1,3 butadiene are obtained, corresponding to an increase in the overall yield of the plant equal to +71.5% with respect to the case without dehydrogenation of the raffinate 1, with the same $C_4$ mixture fed.

EXAMPLE 2

Figure 3:
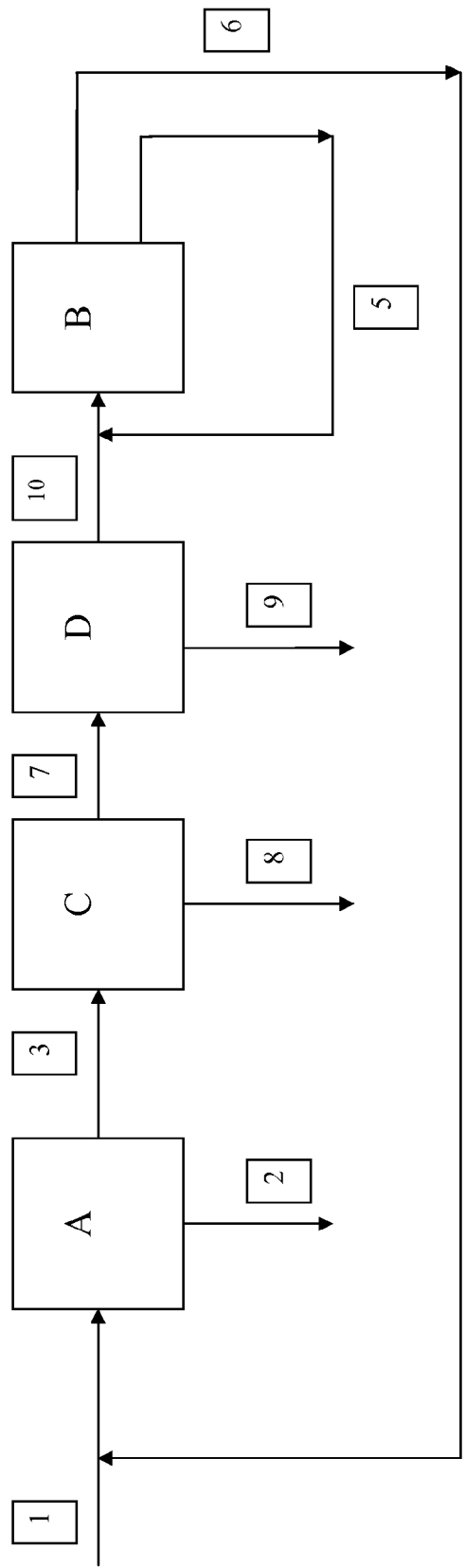
FIG. 3 illustrates an embodiment of the present invention wherein, in addition to the elements and streams identical to those of FIG. 1 and FIG. 2, D is a purification section of 1-butene, 9 is the stream of 1-butene after purification, 10 is the raffinate 3.

The overall yield to 1,3 butadiene of an integrated system comprising an extractive distillation plant of 1,3 butadiene is determined hereunder, starting from a mixture of $C_4$ paraffins and olefins from a steam cracker, a plant for the production of Methyl Tert Butyl Ether MTBE (or Ethyl Tert Butyl Ether ETBE) starting from the raffinate product, leaving extractive distillation, and methanol (or ethanol), a recovery plant of 1-butene starting from the raffinate 2 and a dehydrogenation plant for upgrading the raffinate 3 by recycling a dehydrogenated stream rich in 1,3 butadiene to the extraction section, according to a scheme described hereunder and illustrated in FIG. 3.

A mixture of $C_4$ olefins and paraffins produced by a steam cracker is fed to the extraction unit of 1,3 butadiene and the raffinate product leaving this section is subsequently fed to a MTBE (or ETBE) production unit by reaction with methanol (or ethanol), from which a stream of raffinate 2 is obtained, which is fed to a subsequent section for the recovery of 1-butene. The stream of raffinate 3 leaving the recovery section of 1-butene is sent to a dehydrogenation section, producing a stream rich in butadiene, which is recycled to the extraction unit, and a stream of non-reacted butanes and butanes which is recycled to the dehydrogenation reactor, except for a modest purge of $C_{5+}$ compounds.

Considering a $C_4$ mixture in the feedstock to the plant with the composition of the stream indicated in Table 1 and a flow-rate equal to 33.8 t/h, a production equal to 16.5 t/h of 1,3 butadiene, 13 t/h of MTBE, 3.3 t/h of 1-butene and 4.5 t/h of raffinate 3, is obtained, without integration with the dehydrogenation section of the raffinate 3.

In the case of integration of the butadiene extraction unit with the dehydrogenation unit of the raffinate 3 (see FIG. 3), on the other hand, 18.8 t/h of 1,3 butadiene, 13 t/h of MTBE, 4.4 t/h of 1-butene are obtained, corresponding to an increase in the yield to 1,3 butadiene of the plant equal to +13.5% and to 1-butene equal to +33%, with the same $C_4$ mixture fed.

The invention claimed is:

1. A process for the production of 1,3-butadiene, the process comprising:
   a) extracting, by extractive distillation, in an extraction section, an end-product comprising 1,3-butadiene and a raffinate product, starting from mixtures of saturated and unsaturated compounds having from 2 to 10 carbon atoms in the chain;
   b) sending the raffinate product to a dehydrogenation section;
   c) dehydrogenating the raffinate product in the dehydrogenation section in the presence of a dehydrogenation catalyst and an inert product to form a reaction effluent comprising 1,3-butadiene;
   d) recirculating said reaction effluent comprising 1,3-butadiene directly to the extraction section after separating the incondensable compounds.

2. The process of claim 1, wherein, after separating the incondensable compounds, the reaction effluent is separated into a stream enriched in 1,3-butadiene and a stream which comprises the non-reacted saturated and unsaturated compounds having from 2 to 10 carbon atoms in the chain.

3. The process of claim 2, wherein the stream enriched in 1,3-butadiene is recirculated to the extraction section.

4. The process of claim 2, wherein the stream comprising the non-reacted saturated and unsaturated compounds having from 2 to 10 carbon atoms in the chain is recirculated to the dehydrogenation section.

5. The process of claim 1, wherein the raffinate product comprises isobutene and is subjected to etherification with ethanol or methanol to produce ethyl tert butyl ether or methyl tert butyl ether and a refined stream (raffinate 2) which is sent to the dehydrogenation section.

6. The process of claim 5, wherein the raffinate 2 is sent to a purification section of 1-butene generating a stream of 1-butene and a stream of raffinate 3 which is dehydrogenated.

7. The process of claim 1, wherein the dehydrogenation catalyst is a catalytic composition comprising microspheroidal alumina and an active component comprising a mixture comprising Gallium and/or Gallium oxides, Tin and/or Tin oxides, Platinum and/or Platinum oxides, and oxides of alkaline and/or alkaline earth metals.

8. The process of claim 7, wherein the quantity of Platinum and/or Platinum oxides in said catalytic composition is lower than 500 ppm.

9. The process of claim 7, wherein the quantity of Platinum and/or Platinum oxides in said catalytic composition is lower than 99 ppm.

10. The process of claim 1, wherein the dehydrogenation catalyst comprises an amount ranging from 0.1% wt to 33.6% wt of $Ga_2O_3$, from 1 ppm to 99 ppm of platinum, an amount ranging from 0% wt to 5% wt of oxides of alkaline and/or alkaline earth metals and an alumina carrier modified with a quantity of silica ranging from 0.8% wt to 3% wt.

11. The process of claim 7, wherein the gallium oxides are selected from $Ga_2O_3$, $Ga_2O$ and mixtures thereof.

12. The process of claim 7, wherein the tin oxides are selected from $SnO$, $SnO_2$ and mixtures thereof.

13. The process of claim 7, wherein the platinum oxides are selected from $PtO$, $PtO_2$ and mixtures thereof.

14. The process of claim 7, wherein the oxide of alkaline metals is $K_2O$.

15. The process of claim 1, wherein the dehydrogenation section comprises at least one reactor and at least one regenerator of the dehydrogenation catalyst.

16. The process of claim 15, wherein the reactor is of the "Fast Riser" type.

17. The process of claim 1, wherein the mixture of saturated and unsaturated compounds comprises butanes and butenes.

18. The process of claim 6, wherein the dehydrogenation section can be fed by means of the raffinate product, the raffinate 2 or the raffinate 3 or mixtures thereof.

* * * * *